US00PP20024P2

(12) United States Plant Patent
Dekker

(10) Patent No.: US PP20,024 P2
(45) Date of Patent: May 26, 2009

(54) ***CHRYSANTHEMUM* PLANT NAMED 'DEKFABRICE'**

(50) Latin Name: *Chrysanthemum×morifolium*
Varietal Denomination: Dekfabrice

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/156,714

(22) Filed: Jun. 3, 2008

(51) Int. Cl.
*A01H 5/00* (2006.01)

(52) U.S. Cl. ..... Plt./289
(58) Field of Classification Search ..... Plt./289
See application file for complete search history.

*Primary Examiner*—Kent L Bell
(74) *Attorney, Agent, or Firm*—C. A. Whealy

(57) ABSTRACT

A new and distinct cultivar of *Chrysanthemum* plant named 'Dekfabrice', characterized by its pompon-type inflorescences with yellow green-colored ray florets; strong and upright flowering stems; freely flowering habit; early and uniform flowering response; and good postproduction longevity.

2 Drawing Sheets

Botanical designation: *Chrysanthemum×morifolium.*
Cultivar denomination: 'Dekfabrice'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Dekfabrice'.

The new *Chrysanthemum* is a product of a planned breeding program conducted by the Inventor in Hensbroek, The Netherlands. The objective of the breeding program is to create new freely flowering pompon-type *Chrysanthemum* cultivars with green-colored ray floret coloration and excellent postproduction longevity.

The new *Chrysanthemum* originated from a cross-pollination made by the Inventor in Hensbroek, The Netherlands in 2003 of two unnamed proprietary selections of *Chrysanthemum×morifolium,* not patented. The new *Chrysanthemum* was discovered and selected by the Inventor as a flowering plant from within the progeny of the stated cross-pollination in a controlled greenhouse environment in Hensbroek, The Netherlands in April, 2004.

Asexual reproduction of the new *Chrysanthemum* by terminal cuttings in a controlled greenhouse environment in Hensbroek, The Netherlands since May, 2004, has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekfabrice'. These characteristics in combination distinguish 'Dekfabrice' as a new and distinct cultivar of *Chrysanthemum:*

1. Pompon-type inflorescences with yellow green-colored ray florets.
2. Strong and upright flowering stems.
3. Freely flowering habit.
4. Early and uniform flowering response; plants flower about 48 days after the start of photoinductive treatments.
5. Good postproduction longevity; plants maintain good substance for about three weeks in an interior environment.

Plants of the new *Chrysanthemum* differ from plants of the female parent selection in the following characteristics:

1. Plants of the new *Chrysanthemum* are more vigorous than plants of the female parent selection.
2. Plants of the new *Chrysanthemum* are more freely flowering than plants of the female parent selection.

Plants of the new *Chrysanthemum* differ from plants of the male parent selection in the following characteristics:

1. Plants of the new *Chrysanthemum* are more vigorous than plants of the male parent selection.
2. Plants of the new *Chrysanthemum* are more freely flowering than plants of the male parent selection.

Plants of the new *Chrysanthemum* can be compared to plants of the *Chrysanthemum×morifolium* 'Yoko Ono', disclosed in U.S. Plant Pat. No. 12,566. In side-by-side comparisons conducted in Hensbroek, The Netherlands, plants of the new *Chrysanthemum* differed from plants of 'Yoko Ono' in the following characteristics:

1. Plants of the new *Chrysanthemum* were more vigorous than plants of 'Yoko Ono'.
2. Plants of the new *Chrysanthemum* had larger inflorescences than plants of 'Yoko Ono'.
3. Plants of the new *Chrysanthemum* flowered earlier than plants of 'Yoko
4. Plants of the new *Chrysanthemum* had lighter-colored ray florets than plants of 'Yoko Ono'.

BRIEF DESCRIPTION OF THE PHOTOGRAPHS

The accompanying colored photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*. The photograph on the first sheet comprises a side perspective view of a typical flowering stem of 'Dekfabrice' grown as a spray type. The photograph on the second sheet comprises close-up views of the upper and lower surfaces of typical inflorescences and leaves of 'Dekfabrice'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the winter and early spring in Hensbroek, The Netherlands, under commercial practice in a glass-covered greenhouse. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were nine weeks from planting when the photographs and the description were taken.

Botanical classification: *Chrysanthemum×morifolium* 'Dekfabrice'.

Parentage:

*Female, or seed, parent.*—Unnamed proprietary selection of *Chrysanthemum×morifolium,* not patented.

*Male, or pollen, parent.*—Unnamed proprietary selection of *Chrysanthemum×morifolium,* not patented.

Propagation:

*Type.*—Terminal vegetative cuttings.

*Time to initiate roots.*—About four to six days at 20° C.

*Time to produce a rooted young plant.*—About 13 to 15 days at 20° C.

*Root description.*—Fine, fibrous; light brown in color.

*Rooting habit.*—Freely branching, moderately dense.

Plant description:

*Appearance/growth habit.*—Herbaceous pompon-type cut flower that is typically grown as a spray-type. Moderately vigorous growth habit.

*Flowering stem description.*—Aspect: Erect. Length: About 60 cm. Spray diameter: About 20 cm to 25 cm. Diameter: About 5 mm to 7 mm. Lateral branch length: About 14 cm to 25 cm. Internode length: About 2 cm to 2.5 cm. Texture: Finely pubescent; longitudinally ridged. Color: Close to 146B.

*Foliage description.*—Arrangement: Alternate; simple. Length: About 8 cm to 15 cm. Width: About 4.5 cm to 9 cm. Apex: Obtuse to acute. Base: Attenuate. Margin: Palmately lobed; sinuses parallel to divergent. Texture, upper and lower surfaces: Pubescent, slightly rough; veins prominent on lower surface. Venation pattern: Pinnate, reticulate. Color: Developing foliage, upper surface: Close to 137A. Developing foliage, lower surface: Close to 147B. Fully expanded foliage, upper surface: Close to 147A; venation, close to 146A. Fully expanded foliage, lower surface: Close to 147B; venation, 146B. Petiole: Length: About 1 cm to 2 cm. Diameter: About 2 mm to 4 mm. Texture, upper and lower surfaces: Slightly rough. Color, upper surface: Close to 146B. Color, lower surface: Close to 146C.

Inflorescence description:

*Appearance.*—Pompon-type inflorescence form with oblong-shaped ray florets. Inflorescences borne on terminals, arising from leaf axils. Ray and disc florets develop acropetally on a capitulum. Inflorescences moderately fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about 48 days later when grown as a spray-type.

*Postproduction longevity.*—In an interior environment, inflorescences and foliage will maintain good color and substance for about three weeks. Inflorescences persistent.

*Quantity of inflorescences.*—Freely flowering habit; when grown as a spray type, about 35 inflorescences per flowering stem develop.

*Inflorescence size.*—Diameter: About 3.5 cm. Depth (height): About 1.5 cm. Disc diameter: About 3 mm. Receptacle height: About 5 mm. Receptacle diameter: About 8 mm. Receptacle color: Close to 145B.

*Inflorescence buds.*—Shape: Flattened spherical. Height: About 5 mm. Diameter: About 6 mm. Color: Close to 137C.

*Ray florets.*—Length: About 1 cm to 1.5 cm. Width: About 4 mm to 6 mm. Shape: Oblong; incurved. Apex: Obtuse. Base: Attenuate. Margin: Entire. Angle: Initially upright to close to about 90° from vertical. Texture, upper and lower surfaces: Smooth, glabrous; satiny. Number per inflorescence: About 225 arranged in about 15 whorls. Color: When opening, upper surface: Close to 154A. When opening, lower surface: Close to 150A. Fully opened, upper surface: Close to 154A to 154B. Fully opened, lower surface: Close to N144B; color becoming closer to 154A with development.

*Disc florets.*—Shape: Fused tubular, elongated. Apex: Dentate. Length: About 4 mm to 5 mm. Diameter: About 1 mm. Number per inflorescence: About 15, massed at the center. Color, immature: Apex: Close to 145A. Mid-section: Close to 12A. Base: Close to 145B. Color, mature: Apex: Close to 5A. Mid-section: Close to 154D. Base: Close to 145C.

*Involucral bracts.*—Length: About 5 mm to 8 mm. Width: About 2.5 mm to 5 mm. Shape: Oblong. Apex: Obtuse. Base: Obtuse to truncate. Margin: Entire. Texture, upper and lower surfaces: Smooth, glabrous. Number per inflorescence: About 25 arranged in about three whorls. Color, upper surface: Close to 143A. Color, lower surface: Close to 137C.

*Peduncles.*—Length: About 5 cm to 9 cm. Diameter: About 3 mm. Angle: Erect to about 30° from vertical. Strength: Moderately strong to strong. Texture: Slightly pubescent; longitudinally ridged. Color: Slightly darker than 144A.

*Reproductive organs.*—Androecium: Not observed. Gynoecium: Present on both ray and disc florets. Style length: About 4 mm. Style color: Close to 2A. Stigma color: Close to 9A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekfabrice' as illustrated and described.

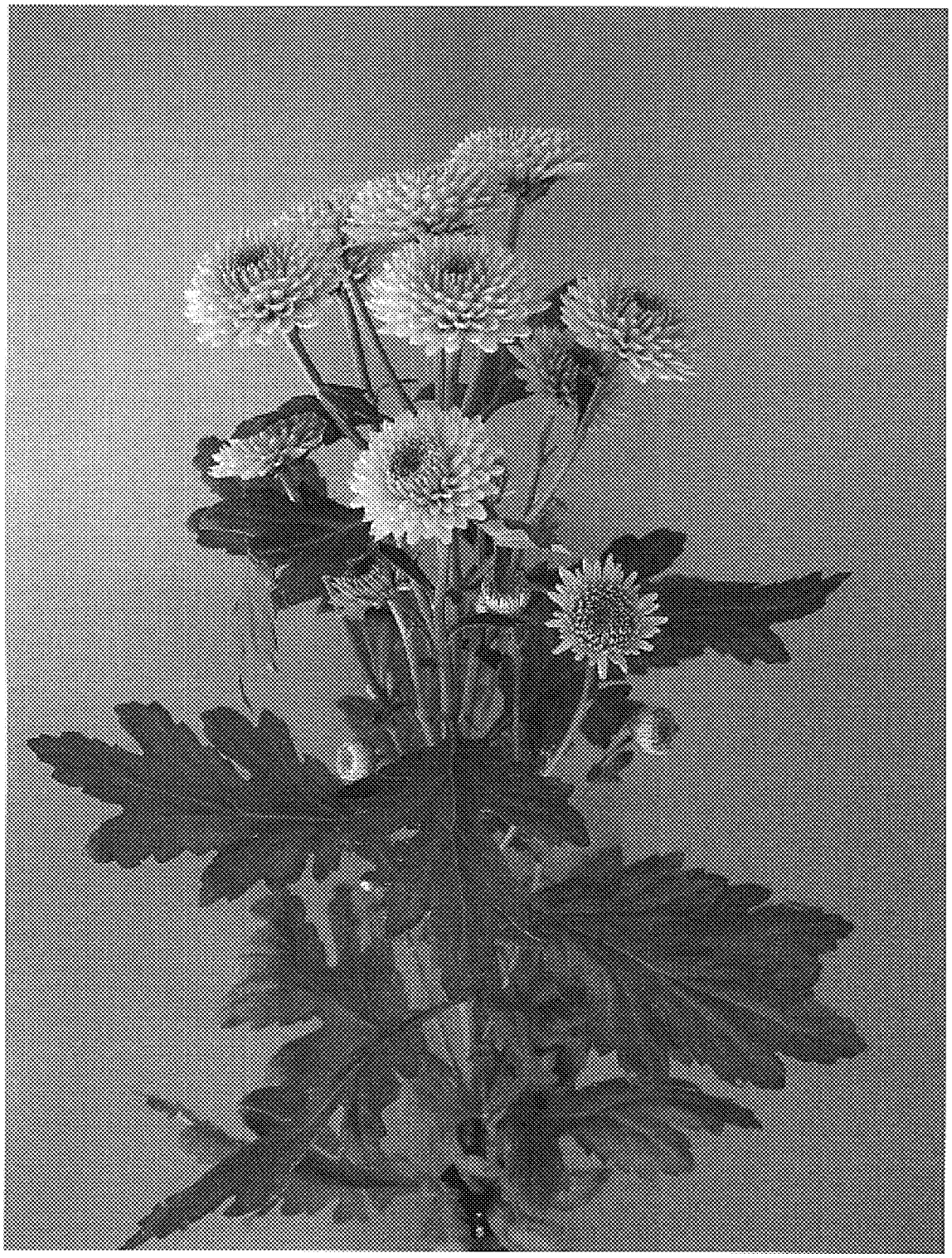

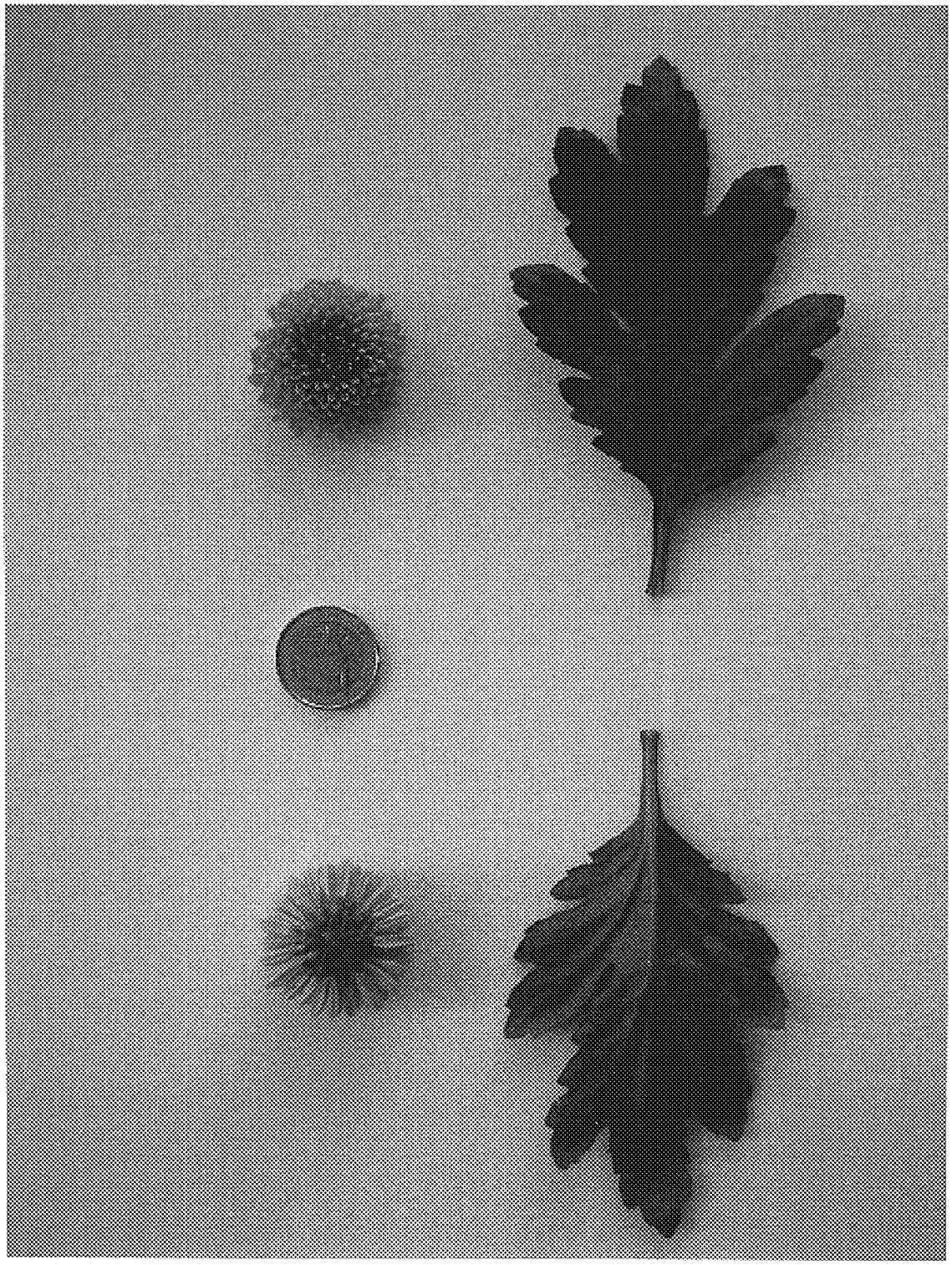

* * * * *